United States Patent
Mehta et al.

(10) Patent No.: US 6,355,258 B1
(45) Date of Patent: Mar. 12, 2002

(54) METHOD FOR FORMULATING SPILL RESISTANT PHARMACEUTICAL COMPOSITIONS IN SEMI-SOLID FORM

(75) Inventors: Rakesh Mehta, Nanuet; Dan Moros, Larchmont, both of NY (US)

(73) Assignee: Taro Pharmaceutical Industries Ltd. (IL)

(*) Notice: Subject to any disclaimer, the term of this patent is extended or adjusted under 35 U.S.C. 154(b) by 0 days.

(21) Appl. No.: 09/548,927

(22) Filed: Apr. 13, 2000

Related U.S. Application Data (62) Division of application No. 09/089,360, filed on Jun. 3, 1998, now Pat. No. 6,071,523.

(51) Int. Cl.⁷ .................................................. A61K 9/00
(52) U.S. Cl. ........................ 424/400; 424/401; 514/781
(58) Field of Search ................................. 424/400, 401; 222/142, 212, 153.06; 414/18, 114, 115; 514/781

(56) References Cited

U.S. PATENT DOCUMENTS

| | | |
|---|---|---|
| 1,466,043 A | 8/1923 | Graham |
| 1,544,232 A | 6/1925 | Huntoon |
| 2,252,119 A | 8/1941 | Edmonds |
| 2,556,571 A | 7/1951 | Boggs et al. |
| 2,559,070 A | 7/1951 | Goldberg |
| 3,104,032 A | 9/1963 | Hansen |
| 3,116,152 A | 12/1963 | Smith et al. |
| 3,133,679 A | 5/1964 | Brown |
| 3,145,886 A | 8/1964 | Goodwin |
| 3,383,018 A | 5/1968 | Grimsley |
| 3,395,835 A | 8/1968 | Tarran |
| 3,493,146 A | 2/1970 | Conners et al. |
| 3,767,784 A | 10/1973 | Gluck |
| 3,797,704 A | 3/1974 | Dykes |
| 3,920,819 A | 11/1975 | Stephens et al. |
| 3,927,205 A | 12/1975 | Ohno et al. |
| 4,091,965 A | 5/1978 | Gebhard |

(List continued on next page.)

FOREIGN PATENT DOCUMENTS

| | | | |
|---|---|---|---|
| EP | 0 189 722 | 8/1986 | |
| EP | 0 379 147 B1 * | 7/1990 | |
| EP | 0 479 005 | 4/1992 | |
| EP | 0 614 659 A3 * | 9/1994 | |
| EP | 0 614 659 A2 * | 9/1994 | |
| EP | 9 815 854 A1 | 1/1998 | ............ A61K/9/48 |
| EP | 0 839 517 A2 | 5/1998 | ............ A61K/7/16 |
| GB | 798900 | 7/1958 | |
| JP | 45-798 | 1/1970 | |
| WO | 96/23486 | 8/1996 | ............ A61K/9/00 |

Primary Examiner—Thurman K. Page
Assistant Examiner—Brian K. Seidleck
(74) Attorney, Agent, or Firm—Venable; Michael A. Gollin

(57) ABSTRACT

A spill-resistant pharmaceutical formulation for oral administration from a squeezable container comprises a pharmaceutical agent in a suitable vehicle comprising a liquid base and a thickening agent, the formulation consisting of mutually compatible components and having the following proper ties: a viscosity within the range of about 7500 to about 12,500 cps using a Brookfield Viscometer with a 'C' spindle with Helipath movement at a spindle speed of 20 rpm and 20–25° C., a viscometric yield value of a semi-solid, a spill-resistant consistency permitting the composition to be squeezed by light manual pressure through a channel, to spread in a spoon bowl sufficiently quickly for accurate measurement, and to remain in the spoon bowl without spilling on spoon inversion, tilting at 90 degrees, and vibration, homogeneity such that the components do not separate under conditions of use, and a storage stability such that the foregoing properties are retained for at least two years shelf life. A method for producing a formulation for a spill-resistant pharmaceutical composition comprises combining a per-unit dose effective amount of a pharmaceutical agent with suitable vehicle components comprising a liquid base and a thickening agent and testing the formulation for acceptance criteria.

22 Claims, 3 Drawing Sheets

U.S. PATENT DOCUMENTS

| | | |
|---|---|---|
| 4,284,649 A | 8/1981 | Wiczer |
| 4,305,933 A | 12/1981 | Wiczer |
| 4,361,580 A | 11/1982 | Peck et al. |
| 4,383,993 A | 5/1983 | Hussain et al. |
| 4,394,390 A | 7/1983 | Hussain et al. |
| 4,427,681 A * | 1/1984 | Munshi |
| 4,540,572 A | 9/1985 | Seth |
| 4,576,645 A * | 3/1986 | Ravel et al. |
| 4,593,048 A | 6/1986 | Sato et al. |
| 4,651,905 A | 3/1987 | Hayes |
| 4,724,615 A | 2/1988 | Mackles et al. |
| 4,761,400 A | 8/1988 | Doat et al. |
| 4,830,222 A | 5/1989 | Read |
| 4,883,660 A | 11/1989 | Blackman et al. |
| 4,957,226 A | 9/1990 | Pacia |
| 4,964,538 A | 10/1990 | Nimmey et al. |
| 5,137,183 A | 8/1992 | Mikulec et al. |
| 5,154,926 A | 10/1992 | Kawaski et al. |
| 5,288,479 A * | 2/1994 | Gorman et al. |
| 5,300,302 A | 4/1994 | Tachon et al. |
| 5,305,928 A | 4/1994 | Verdagurer |
| 5,602,182 A | 2/1997 | Popli et al. .......... 514/653 |
| 5,881,926 A * | 3/1999 | Ross |

\* cited by examiner

METHOD FOR FORMULATING SPILL RESISTANT PHARMACEUTICAL COMPOSITIONS IN SEMI-SOLID FORM

This application is a Divisional of U.S. application Ser. No. 09/089,360, filed Jun. 3, 1998, now U.S. Pat. No. 6,071,523.

BACKGROUND OF THE INVENTION

The invention relates to compositions for administering pharmaceuticals orally without spilling. More specifically, the invention relates to vehicles and devices for delivering a variety of pharmaceutical products.

Syrups, elixirs, solutions, and suspensions are traditional dosage forms for oral medication. These liquid formulations are typically measured by pouring into a spoon, but this approach has the great drawback of spillage. The risk of spillage can cause people to underfill the spoon, leading to inaccurate dosage. With elderly people, children, and the infirm, difficulty in filling a spoon with a liquid and bringing it to the mouth can be a serious impediment to administering the medicine. Solid formulations such as pills, tablets, and capsules are also difficult for children and for elderly, infirm people to swallow.

Tachon et al., U.S. Pat. No. 5,300,302, teaches a pump dispenser for administering a metered dosage of a drug formulation. This requires a complex mechanical device and formulation properties suitable for pumping.

Gorman et al., U.S. Pat. No. 5,288,479, teaches a thickened pharmaceutical preparation comprising a hexitol and a seaweed polysaccharide. Such compositions tend to separate, and require a meter dispenser.

Ross, U.S. Ser. No. 08/114,315, now U.S. Pat. No. 5,881,926, EP 95939059.2 (commonly owned with this application and incorporated herein by reference), teaches semi-solid formulations and a delivery system. However, there remains a need for more stable compositions with improved rheological characteristics. There is also a need for a reliable test system for identifying optimal formulations.

SUMMARY OF THE INVENTION

The invention relates to a drug delivery system including a combination of a squeezable container, a dispenser, and a semi-solid pharmaceutical formulation. Each of these elements of the drug delivery system has certain characteristics so that the combination (a) allows easy administration (b) of a measured amount of the drug, (c) from a convenient, preferably tamper-resistant and child-proof container, (d) with predetermined resistance to spilling, (e) while providing a suitable storage stable pharmaceutical composition with compatible components. These properties result from a variety of physico-chemical characteristics of the formulation optimized in conjunction with the type of container and dispenser.

An embodiment of the invention is a method for obtaining a suitable spill-resistant formulation comprising combining a systemic pharmaceutical agent suitable for oral administration with a semi-solid vehicle, and then conducting the following tests of the formulation: measuring initial viscosity, measuring yield value, extruding the formulation into a spoon from a container through a 1 to 5 mm orifice, observing the spreading/leveling characteristic of the formulation in the spoon, measuring spill resistance by spill start time after at least one of spoon vibration, spoon inversion, and soon tilting at 90 degrees, and measuring viscosity after storing at elevated temperature for at least one month.

The compositions of the invention are light, water-soluble gels, which are easy to clean from a spoon bowl, and from any other surfaces which they may contact. The surface tensions of the formulations are sufficiently high to provide desirable spill-resistance, while allowing the product to be sufficiently free-flowing. In the examples of the prior Ross application, the viscosity was higher, providing a firm, spill-proof product. Here, the range of viscosity is lower, providing a freer-flowing, better leveling product, that is easier to administer with spill-resistance, but one which is more prone to spillage than the prior formulations. Thus, while the prior compositions may be considered spill-proof, the compositions set forth here are optimally "spill-resistant" but have other superior characteristics e.g. as to measurability and dispensability.

Preferred characteristics for the formulation and the method are as follows. The viscosity, when measured by a Brookfield Viscometer using "C" spindle at 20 rpm and 20–25 degrees Celsius, is between about 5,000 to 50,000 cps, preferably less than 25,000 cps. Surprisingly, a most preferred range for a formulation to be squeezed from a tube is between about 7,000 and about 12,500 cps. The formulation does not start to spill until after about 30 seconds when vibrated at a frequency of about 2–8 per second, and an amplitude up to about 1 inch. The spill start time on spoon inversion is at least about 20–30 seconds for a plastic 8 ml spoon, longer than for a syrup, an within about 1–20 seconds on spoon tilting at 90 degrees, which is slower than a syrup, but faster than prior non-spill formulations.

Preferred compositions have good shelf life, meaning that the preferred characteristics are retained after at least three months storage at a temperature of at least about 40 degrees Celsius at 75% humidity, which extrapolates under normal assumptions accepted by the U.S. Food and Drug Administration to two years shelf-life stability at room temperature. Surprisingly, in preferred embodiments using carboxyvinyl polymers such as Carbopol 974, stability may be accomplished by minimizing sodium containing substances from the formulation. Also, the Carbopol has a surprising taste masking effect for bitter drugs like acetaminophen.

Preferred compositions have Carbopol 974 in a concentration of from about 0.25% to below about 1%, in contrast to prior compositions having 1% or more. Other preferred compositions ha e a cellulose derivative in an amount of from about 2.5% to 3.3%, more preferably less than about 2%. A particularly preferred composition has about 1% microcrystalline cellulose and less than about 2.0% sodium carboxymethylcellulose, in contrast to prior formulations with about 2.4 to 2.8% CMC.

The configuration of the container, closure device, and receptacle and the consistency of the formulation are selected so that in response to pressure on the container when the channel closure device open, a single predetermined unit dose of the pharmaceutical composition can be easily squeeze by manual pressure from the container through the channel into the receptacle, measured, and administered orally without spilling any of the composition from the container or the receptacle. The device may be as shown in the commonly owned Ross application or any other suitable device available to a person of ordinary skill.

This invention succeeds where previous efforts failed to provide a simple, stable, useful system of spill-resistant pharmaceutical formulations. This invention solves a previously unrecognized problem as to the rheological properties that must be optimized for a successful spill-resistant formulation.

This invention is in a crowded and mature art of oral medications, in which new dosage forms are constantly sought, at great expense and at high profit. Nonetheless, no similar composition or system has been previously discovered. Indeed, semi-solid formulations run contrary to the conventional wisdom of using either liquid or solid dosage forms.

This invention omits complex mechanical elements employed in the prior art such as pumps, syringes, and elaborate measuring vessels without loss of ability, and indeed with improved performance. This provides advantages in manufacturing, distribution, and waste disposal, and other economies as well.

The drug delivery system of the invention is counter-intuitive and inventive as indicated by the lack of commercially available embodiments of semi-solid formulations for oral administration of pharmaceutical agents. The resistant drug delivery system of the invention solves such longstanding problems with liquid formulations as spillage, and resultant underfilling of measuring spoons. The drug delivery system of the invention also overcomes the disadvantages of solid dosage forms, such as being hard to swallow.

The inventive formulations are semi-solid, not liquid or solid. Palatability, stability (a long shelf life) compatibility of components, and ease of administration of a required dose are provided. The system allows effortless administration of predetermined measured doses to children and adults with motor problems, without spilling. It is easier to measure than a liquid and easier to swollow than a solid.

A spill-resistant pharmaceutical formulation for oral administration from a squeezable container comprises a per-unit dose effective amount of a pharmaceutical agent in a suitable vehicle comprising a liquid base and a thickening agent, the formulation consisting of mutually compatible components and having the following properties: a viscosity within the range of about 7500 to about 25,000 cps using a Brookfield Viscometer with a 'C' spindle with Helipath movement at a spindle speed of 20 rpm and 20–25° C.; a viscometric yield value of a semi-solid; a spill-resistant consistency permitting the composition to be squeezed by light manual pressure through a channel of about 1–5 mm, to spread in a spoon bowl sufficiently quickly for accurate measurement, and to remain in the spoon bowl without spilling for at least several seconds on spoon inversion and tilting at 90 degrees, and for at least one minute upon spoon vibration; homogeneity such that the components do not separate under conditions of use, and a storage stability such that the foregoing properties are retained for at least three months of storage at accelerated stability conditions of elevated temperature and humidity.

The viscosity is preferably between about 7000 and about 25,000 cps, more preferably between about 7500 and about 12,500 cps, after storage for three months at a temperature of at least 40 degrees The formulation preferably comprises about 0.25 to about 1% water-soluble carboxyvinyl polymer and is referably essentially free of sodium. The liquid base preferably comprises glycerin and sorbitol, and the thickening agent preferably comprises sodium carboxymethylcellulose in an amount of less than about 2.5% and microcrystalline cellulose in an amount of about 0.9%. The formulation preferably comprises glycerin and sorbitol as a solution of about 70% in water, the concentration of glycerin and sorbitol solution being about 40%, and microcrystalline cellulose in an amount of about 0.9%, and carboxymethylcellulose in an amount of about 0.9% to 2.4%.

The pharmaceutical agent is preferably selected from the group consisting of an analgesic, non-steroidal anti-inflammatory, antihistamine, cough suppressant, expectorant, bronchodilator, anti-infective, CNS active drug, cardiovascular drug, antineoplastic, cholesterol-lowering drug, anti-emetic, vitamin, mineral supplement and fecal softener. The pharmaceutical agent may be selected from e group consisting of acetaminophen, aspirin, ibuprofen, diphenhydramine, dextromethorphan, guafenesin, pseudoephedrine, carbidopa, levodopa, terfenadine, ranitidine, ciprofloxacin, tiazolam, fluconazole, propranolol, acyclovir, fluoxetine, enalapril, diltiazem, lovastatin and a pharmaceutically acceptable salt or ester thereof.

The liquid base is preferably in an amount of about 45 weight-percent to about 95 weight-percent, comprising a palatable solvent, selected from the group consisting of water, propylene glycol, polyethylene glycol, glycerin, and mixtures thereof, and the thickening agent is preferably in amount of about 1 weight-percent to about 55 weight-percent, and is selected from the group consisting of starch, modified starch, sodium carboxymethyl cellulose in an amount of less than about 2%, microcrystalline cellulose, hydroxypropyl cellulose, other cellulose derivatives, acacia, tragacanth, pectin, gelatin, polyethylene glycol, and water-soluble carboxyvinyl polymers in a concentration of less than 1% and in the absence of a sodium component. The thickening agent is preferably a cellulose derivative in an amount of about 0.9 to 2.5 weight % by volume.

The invention further encompasses a pharmaceutical delivery system comprising the formulation of the invention in a squeezable container from which a unit dose of the formulation may be squeezed, either a single dose or multiple doses of the formulation. The system may further comprise a spoon bowl receptacle attachable to the container.

A method for producing a formulation for a spill-resistant pharmaceutical composition comprises combining a per-unit dose effective amount of a pharmaceutical agent with suitable vehicle components comprising a liquid base and a thickening agent, testing the formulation for acceptance criteria for a composition that can be easily squeezed from a container into a receptacle, measured, and administered orally without spilling the composition from the container or the receptacle, and accepting a formulation that satisfies the acceptance criteria, the acceptance criteria comprising:

viscosity within the range 2500–75,000, preferably 5000–45,000 cps equivalent using a Brookfield Viscometer with a 'C' spindle with Helipath movement at 20 RPM and 20–25° C.;

viscometric yield value, ease of administration comprising (a) extrudability under light manual pressure from a squeezable container or a proxy (e.g. a syringe with a 5 mm orifice), and (b) spreadability in a spoon bowl measured by extruding the formulation into a spoon bowl and determining whether the material spreads to the edges of the spoon bowl, spill resistance in the spoon bowl during at least one test period of vibrations, inversion, and tilting, while monitoring whether the product spills from the spoon, mutual compatibility of the components such that they do not separate, and shelf-life of two years at room temperatures as demonstrated by 3-months accelerated stability testing at elevated temperature and humidity.

The test spoon may be plastic and the test period for vibrations at least about five minutes, the test period for inversion at least about 30 seconds, and the test period for tilting at least about 20 seconds. The spreadability is such that the formulation spreads to the edge of the spoon within seconds. The method preferably comprises testing a vehicle without the pharmaceutical agent for at least one of the acceptance criteria, combining the pharmaceutical agent with the vehicle, and then testing the formulation for all acceptance criteria.

Further objectives and advantages will become apparent from a consideration of the description and drawings.

BRIEF DESCRIPTION OF THE DRAWINGS

The invention is better understood by reading the following detailed description with reference to the accompanying figures, in which like reference numerals refer to like elements throughout, and which:

FIGS. 1–4 were included in the commonly-owned Ross application.

FIG. 5 illustrates inventive test equipment.

DETAILED DESCRIPTION OF THE PREFERRED EMBODIMENTS

In describing preferred embodiments of the present invention illustrated in the drawings, specific terminology is employed for the sake of clarity. However, the invention is not intended to be limited to e specific terminology so selected, and it is to be understood that each specific element include all technical equivalents which operate in a similar manner to accomplish a similar purpose.

Oral drug delivery systems are typically either liquid or solid dosage forms. The invention provides a new system combining a squeezable container and a semisolid oral dosage formulation. There has been longstanding need for such a system, and there is nothing like it available. This system include a formulation that has certain physico-chemical and rheological characteristics: such a formulation is (a) semisolid, (b) spill-resistant, (c) easy to administer and measure, (d) storage stable, (e) comprised of compatible components, and (f) has viscosity within a specific range. The meaning of these terms is apparent to one experienced with drug formulation, and as defined herein.

Viscosity is measured using a Brookfield Viscometer with a 'C' spindle with Helipath movement at 20 RPM and 20–25° C., or equivalent. Viscosity decreases slightly with increasing temperature. It has been noted that viscosity measured at 10 rpm may be significantly higher (50–100%) than measured at 20 rpm; however for some of the formulations, it is impossible to measure the viscosity accurately at, the slower spindle speed. It was therefore determined that the 20 rpm spindle speed gave a better reflection of the important rheologic properties of the inventive formulations.

Semi-solid character is used to indicate a formulation that has a viscometric yield value determined as a relative value, e.g. using the shutting off motion of a Brookfield Viscometer with dial gauge.

Ease of administration is intended to mean (a) extrudability under light manual pressure from a squeezable container or a proxy (e.g. a syringe with a 5 mm orifice), and (b) spreadability in a spoon bowl measured by extruding the formulation into a spoon bowl and determining whether the material spreads to the edges of the spoon bowl.

Spill resistance is meant as something different than non-spill characteristics. A spill-resistant formulation according to the invention begins to spill from a spoon bowl during test periods of vibrations, inversion, and tilting, but slowly enough to conform with practical time limits between dispensing and ingesting, and quickly enough to enable the product to be readily consumed from a spoon bowl.

Mutual compatibility of the components means that they do not separate in preparation and storage for the equivalent of two years at room temperature (as indicated by three-months accelerated stability testing at 40° centigrade and 75% relative humidity). Storage stability means that the materials do not lose their desirable properties during storage for the same period. Preferred compositions do not exhibit a drop in viscosity of more than 50% or an increase in viscosity of more than 100% during that period.

Only certain formulations may be prepared to have the physico-chemical and rheological characteristics described herein rendering them suitable for the drug delivery system of the application. Other formulations lack the critical characteristics and are therefore distinct.

Criteria for selecting formulations according to the invention included the following:

they are semi-solid, in that they have a viscometric yield value determined as a relative value, e.g using the shutting off motion of a Brookfield Viscometer with dial gauge.

They are easy to administer—they were easily squeezed from a tube into a teaspoon with light manual pressure such as could be applied by an elderly or infirm person; they tended to level themselves in the spoon by spreading to the edge of the spoon to allow accurate measurement of a teaspoon dose; they did not spill quickly when the spoon was shaken, tipped, or inverted; and they had a consistency making them readily removed orally from the spoon (when a subject inserted the spoon into his mouth, closed his lips, and removed the spoon).

They are spill-resistant—this characteristic was quantified in experiments emulating the behavior of elderly, infirm, and young people, in which full teaspoon samples of the formulations were shaken, tilted, and inverted.

They are storage-stable for an extended period, without any evidence of separation, hardening, or softening; they retain their preferred viscosity range.

They have attractive appearance, suitable texture and mouthfeel.

The components are mutually compatible in that they do not interfere with the bioactivity of the pharmaceutical agent or physical properties of the vehicle, and the components do not separate and retain their properties.

The formulations are suitable for a squeezable container such as a tube, and for extrusion into a receptacle such as a spoon bowl. The receptacle is sized to hold a unit dose, to hold it conveniently without spilling, and to be comfortable and provide a good fit into the mouth between the lips for oral administration. The oval sectional shape of a typical teaspoon bowl as evolved over history satisfies these criteria and is a suitable receptacle, although other shapes can work as well.

These properties complement the characteristics of a simple preferably tamper-resistant and childproof dispensing system for a storage stable, semi-solid, spill-resistant oral systemic pharmaceutical that is easy to administer and measure.

EXAMPLES

To compare the drug delivery system of the invention to other technologies, experiments were conducted with the goal of identifying and quantifying the relevant physico-chemical characteristics of formulations according to the invention. These were compared to characteristics of other formulas that are commercially available or disclosed in the prior art. The results indicate that the properties of the pharmaceutical compositions herein have surprising advantages and critical characteristics necessary for a non-spill drug delivery system and that the other tested products are unsatisfactory for this system.

Material, and Methods

TEST SAMPLES (Examples 21 to 31): Laboratory scale (100 g–500 g) batches of pharmaceutical formulations were prepared essentially according to the methods and compositions described in examples 2–4, 7, 9, 11–13, 15–16, and 18 of the earlier Ross application, U.S. Ser. No. 08/114,315. These compositions were tested for the new acceptance criteria set forth herein. These formulations have liquid bases in a concentration of from about 45% to about 97%, and thickeners in range of 1% for Carbomer, 2–3% for cellulose derivative, or 45% for polyethylene glycol (PEG).

S.N. 21

Example 2

Pseudoephedrine HCl Formulation Thickened with Polyethylene Glycols

| Ingredient | % |
| --- | --- |
| Pseudoephedrine HCl | 0.6 |
| Propylene Glycol | 25.0 |
| Polyethylene Glycols (PEG 400:PEG 3350 3:1) | 73.5 |
| Methyl Paraben | 0.22 |
| Sodium Saccharin | 0.20 |
| Strawberry Flavor | 0.05 |
| D&C Red #33 | 0.0057 |
| Purified water to | 100 |

PEG with a molecular weight less than 800 is a solid and works as a thickener and over 800 is a liquid. Thus, in S.N. 21, about 18% of the formulation is PEG 3350 (a liquid) and about 55.5% is PEG 400 (a thickener).

S.N. 22

Example 3

Acetaminophen Formulation Thickened with Carboxymethylcellulose

| Ingredient | % |
| --- | --- |
| Acetaminophen | 3.2 |
| Glycerin | 4.0 |
| Propylene Glycol | 25.0 |
| Sodium Saccharin | 0.2 |
| Methyl Paraben | 0.22 |
| Sodium Carboxymethylcellulose | 2.4 |
| Purified water to | 100 |

S.N. 23

Example 4

Dextromethorphan Hydrobromide Formulation Thickened with Carbomer

| Ingredient | % |
| --- | --- |
| Dextromethorphan HBr | 0.3 |
| Propylene Glycol | 25.0 |
| Glycerin | 4.0 |
| Carbomer 974P | 1.0 |
| Strawberry Flavor | 0.05 |
| Sodium Saccharin | 0.2 |
| Sodium Hydroxide (10% Solution) | 1.75 |
| Purified water to | 100 |

S.N. 24

Example 7

(Placebo) Formulation Thickened with Sodium Carboxymethylcellulose

| Ingredient | % |
| --- | --- |
| Citric Acid | 0.200 |
| ETDA Disodium | 0.020 |
| FDC red #33 | 0.006 |
| Glycerin | 20.000 |
| Sodium Carboxymethylcellulose | 2.400 |
| Sodium benzoate | 0.100 |
| Hydrogenated glucose (a thickener) | 6.5 |
| Purified water to | 100 |

S.N. 25

Example 9

(Placebo) Formulation Thickened with Sodium Carboxymethylcellulose and Hydroxypropyl Methylcellulose

| Ingredient | % |
|---|---|
| Dibasic Sodium Phosphate | 0.030 |
| Sodium Carboxymethylcellulose | 2.400 |
| Hydroxypropyl Methylcellulose (F4M) | 0.900 |
| Monobasic Potassium Phosphate | 0.020 |
| Methyl Paraben | 0.180 |
| Propyl Paraben | 0.500 |
| Sodium Chloride | 0.050 |
| Sorbitol 70% | 30.000 |
| Purified water to | 100 |

S.N. 26

Example 11

(Placebo) Formulation Thickened with Sodium Carboxymethylcellulose

| Ingredient | % |
|---|---|
| Sodium Benzoate | 0.250 |
| FDC Yellow #6 | 0.008 |
| Sodium Saccharin | 0.220 |
| Sodium Carboxymethylcellulose | 2.800 |
| Hydrogenated Glucose | 20.000 |
| Purified water to | 100 |

S.N. 27

Example 12

(Placebo) Formulation Thickened with Sodium Carboxymethylcellulose

| Ingredient | % |
|---|---|
| Sodium Carboxymethylcellulose | 2.400 |
| FDC Red #33 | 0.006 |
| Sodium Saccharin | 0.240 |
| Sodium Chloride | 0.050 |
| Purified water to | 100 |

S.N. 28

Example 13

Acyclovir Formulation Thickened with Sodium Carboxymethylcellulose and Microcrystalline Cellulose

| Ingredient | % |
|---|---|
| Acyclovir | 4.000 |
| Methyl Paraben | 0.100 |
| Propyl Paraben | 0.020 |
| Sodium Carboxymethylcellulose | 2.400 |
| Peppermint Flavor | 0.150 |
| Glycerin | 20.000 |
| Microcrystalline Cellulose | 0.900 |
| Sorbitol 70% | 20.000 |
| Sodium Saccharin | 0.30 |
| FDC Yellow #6 | 0.008 |
| Purified water to | 100 |

S.N. 29

Example 15

(Placebo) Formulation Thickened with Sodium Carboxymethylcellulose and Microcrystalline Cellulose

| Ingredient | % |
|---|---|
| FDC Red #33 | 0.006 |
| Microcrystalline Cellulose | 0.900 |
| Sodium Carboxymethylcellulose | 2.400 |
| Methyl Paraben | 0.200 |
| Propyl Paraben | 0.050 |
| Sodium Saccharin | 0.250 |
| Purified water to | 100 |

S.N. 30

Example 16

(Placebo) Formulation Thickened with Sodium Carboxymethylcellulose

| Ingredient | % |
|---|---|
| FDC Red #33 | 0.007 |
| Saccharin Sodium | 0.250 |
| Imitation Cherry Flavor | 0.150 |
| Sodium Carboxymethylcellulose | 2.800 |
| Methyl Paraben | 0.220 |
| Purified water to | 100 |

S.N. 31

Example 18

(Placebo) Formulation Thickened with Sodium Carboxymethylcellulose and Polyethylene Glycol

| Ingredient | % |
| --- | --- |
| Butylhydroxy Toluene | 0.200 |
| Sodium Carboxymethylcellulose | 2.500 |
| Polyethylene Glycol 1500 | 25.000 |
| Methyl Paraben | 0.200 |
| Purified water to | 100 |

REFERENCE SAMPLES (Serial Nos. 32–37): The following commercially available formulations were obtained (Serial Nos. 32–34). These were selected as examples of thick viscous liquid reparations suitable for pharmaceutical use.

S.N. 32

Corsym Antihistaminic Suspension (Manufactured by Ciba, Canada), Containing Phenylpropanolamine Hydrochloride, Chlorpheniramine Maleate, Antifoam A, Corn Syrup, Ethyl Cellullose, Flavoring, Methyl and Propyl Paraben, Polyethylene Glycol, Polysorbate 80, Starch, Vegatable Oil, Xantham Gum, and Water.

S.N. 33

Agarol Laxative Liquid (Manufactured by Warner Lambert Co., Canada), Containing Mineral Oil, Glycerin, Phenolphthalein, Agar, Sodium Cyclamate, and Water.

S.N. 34

Natural Honey

Also several noncommercial pharmaceutical formulations disclosed in prior patents were also prepared Ser. Nos. 35–37) to determine whether the characteristics of the formulations (such as viscosity, semisolid character, non-spillability, ease of administration, storage stability) would be suitable for the drug delivery system of the invention. The formulations were as described in e patents, except the materials were prepared as placebos (without the active ingredient). The characteristics of the formulations should not be expected to be significantly different with the active ingredient. As to Tachon et al. (Nos. 36–37), the two formulations selected were closest to those in the examples herein in that they lacked xanthan gum and other extraneous ingredients.

S.N. 35

Sterling Patent (Gorman et al., U.S. Pat. No. 5.288, 479), Example, Placebo

| Ingredient | % |
| --- | --- |
| PEG-6-32 (PEG 300/PEG 1500 = 1:1) | 20.00 |
| Propylene Glycol | 5.00 |
| Glycerin | 5.00 |
| Sorbitol Solution, 70% | 40.00 |
| Potassium Sorbate | 0.300 |
| Benzoic Acid | 0.100 |
| FD & C Red #33 | 0.010 |
| Cherry/Raspberry Flavor | 0.094 |
| Calcium Saccharin | 0.180 |
| Carrageenan | 1.50 |
| Purified Water to | 100 |

S.N. 36

Nestec Patent (Tachon et al., U.S. Pat. No. 5,300, 302, Example 24, Placebo

| Ingredient | % |
| --- | --- |
| Carbomer 974P | 1.0 |
| Glycerol | 15.0 |
| Sorbitol | 15.0 |
| Methyl paraben | 0.15 |
| Sodium saccarinate | 0.2 |
| Purified water to | 100 |

S.N. 37

Nestec Patent (Tachon et al., U.S. Pat. No. 5,300, 302, Example 31, Placebo

| Ingredient | % |
| --- | --- |
| Carbomer 974P | 1.7 |
| Sodium hydroxide | 0.79 |
| Sodium benzoate | 0.2 |
| Sodium saccharinate | 0.2 |
| Purified water to | 100.00 |

VISCOSITY: To measure viscosity, a Brookfield Viscometer was used with a 'C' spindle with Helipath movement at 20 RPM and 20° C. Further details are given in Table 1.

SEMI-SOLID CHARACTER: If a material is a semisolid then it has a measurable yield value. Yield value was measured as a relative value for all the samples utilizing the shutting off motion of the Brookfield Viscometer (with dial gauge). Semisolid products in gel or other semi-solid form have a significant yield value; thick liquids or suspensions do not. The character of the material can be confirmed by visual and tactile observation.

EASE OF ADMINISTRATION: Ease of administration is reflected both (a) in extrudability and (b) spreadability. Extrudability was measured by loading 8 ml of the product into a syringe having an orifice of about 5 mm or less, then pressing the product out through the orifice. Extrudability is the ease of extruding a product from a squeezable container through a small orifice onto a spoon. A product that is difficult to extrude under these conditions is unsuitable for administration from a squeezable container. Extrudability also reflects the ease of ingesting the formulation when the spoon is placed in the mouth and the tongue is used to remove the product cleanly from the spoon. Spreadability (leveling) was measured by observing the behavior of the product over 5 minutes to determine whether the material remains as a heap or tends to spread to the edges of the spoon. Spreadability is also important to the ability to measure and administer a predetermined dose (typically one teaspoon) of a formulation.

Figure 1:
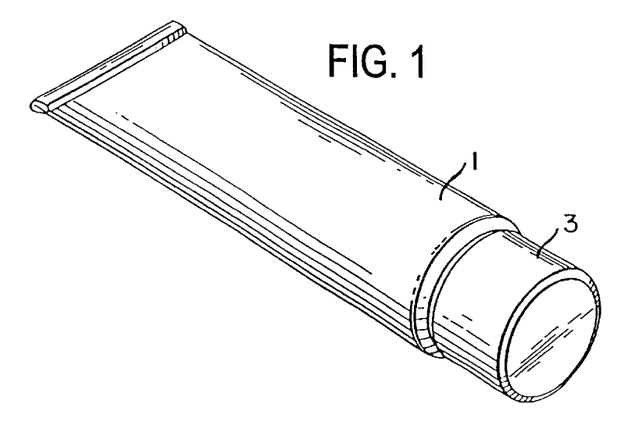
FIG. 1 illustrates a closed tube containing a semisolid composition of the invention
Figure 2:
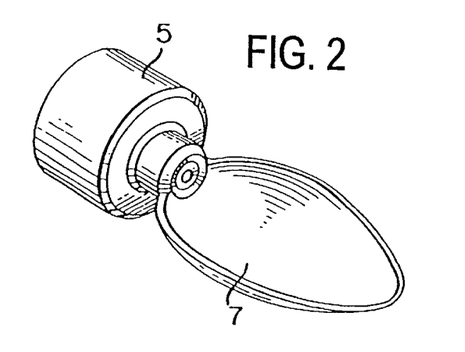
FIG. 2 illustrates a replacement cap of the invention for the tube of FIG. 1 equipped with a spoon for measuring and administering a dose of the semisolid composition of the invention.
Figure 3:
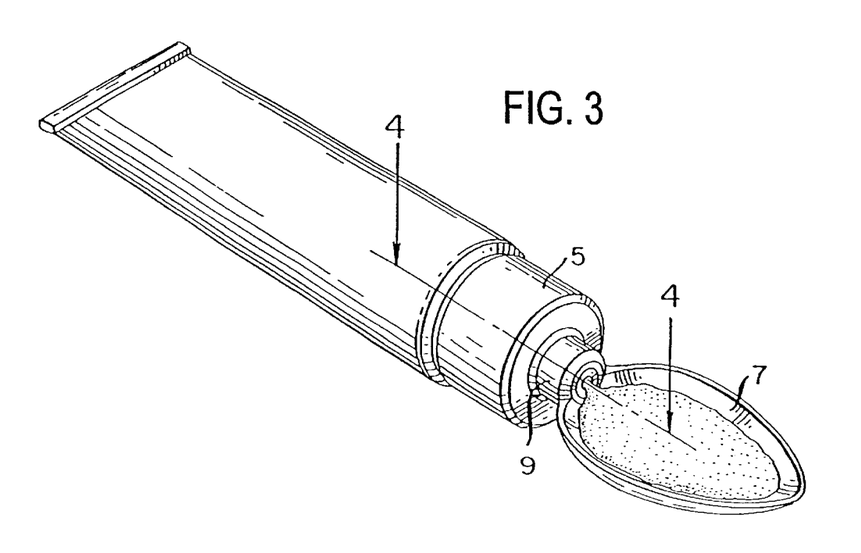
FIG. 3 illustrates a tube containing the semisolid composition of the invention with attached replacement cap equipped with a spoon.
Figure 4:
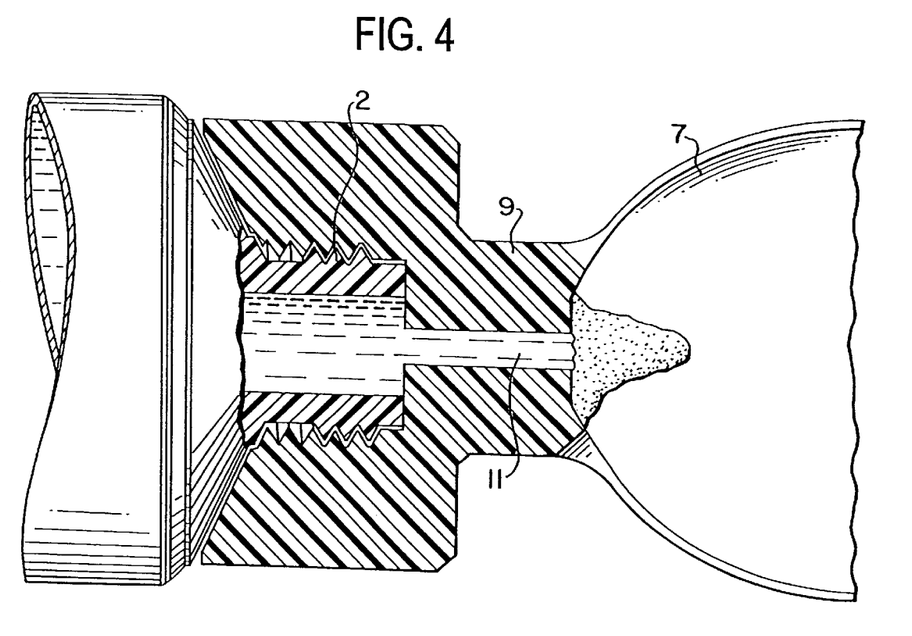
FIG. 4 hows a section of FIG. 3 along lines 4—4.
Figure 5A:
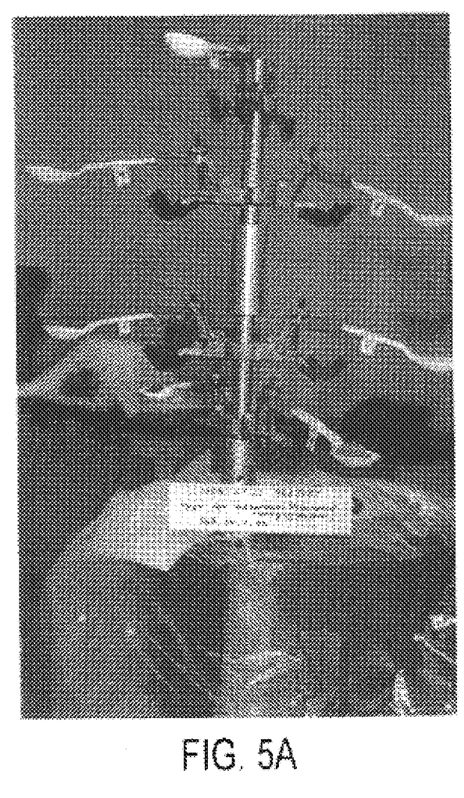
FIG. 5A shows an apparatus for measuring spill resistance on vibration.

SPILL RESISTANCE—VIBRATION: Three components of spill resistance measured:vibrations, inversion, and tilting. As to vibration, a lab shaker with minor modification was used to demonstrate, quantitatively, the extent of non-spillability of the claimed products when shaken in the spoon. The lab shaker was modified to exhibit controlled horizontal motion of the spoon(s) attached. See FIG. 5A.

SPILL RESISTANCE—INVERSION: A custom-made platform was prepared to show the comparative Spilling of the product from a spoon, when inverted (turned upside down).

Figure 5B:
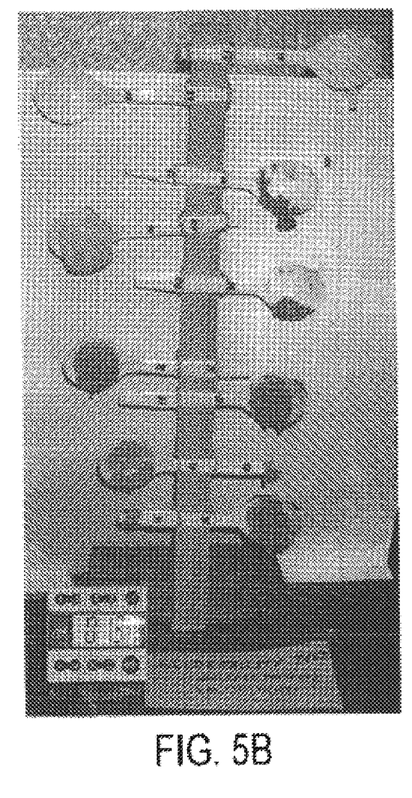
FIG. 5B illustrates an apparatus for measuring spill resistance on tilting at 90 degrees.

SPILL RESISTANCE—TILTING: Measurements were made to determine the time at which the products tend to come off the spoon. The method used was to clamp spoons at a 90° angle and monitor the product sliding off the spoon. See FIG. 5B.

Results

The data generated on the above samples is presented in Tables 1 and 2. The data emphasizes the important properties and advantages of a semi-solid drug delivery system. Table 1 presents the physico-chemical characteristics of the test samples and reference samples. Table 2 presents the spill resistance data.

TABLE 1

PHYSICO-CHEMICAL CHARACTERISTICS

| No. | Product/Base Description | Viscosity (cps) | Semi-solid Characteristics | Ease of Administration** |
|---|---|---|---|---|
| A. Test samples (From Ross Patent Application) | | | | |
| 21 | PEG/PG Base w/Pseudoephed. | 36,500 | Yes | + |
| 22 | CMC/PG/Gly base w/APAP | 38,500 | Yes | ++ |
| 23 | Carbomer/NaOH w/DMH Br | 13,500 | Yes | ++ |
| 24 | CMC/Gly/Hyd. Glucose base (Placebo) | 43,500 | Yes | ++ |
| 25 | CMC/HPMC/Sorbitol base (Placebo) | 45,000 | Yes | ++ |
| 26 | CMC/Hyd. Glucose base (Placebo) | 48,000 | Yes | +++ |
| 27 | CMC base (Placebo) | 28,000 | Yes | ++ |
| 28 | CMC/MCC/Glyc/Sorb. base w/Acyclovir | 45,000 | Yes | +++ |
| 29 | CMC/MCC Base (Placebo) | 24,500 | Yes | ++ |
| 30 | CMC Base (Placebo) | 38,000 | Yes | ++ |
| 31 | CMC/PEG Base (Placebo) | 42,500 | Yes | ++ |
| B. Reference Samples (Commercial products or patented examples) | | | | |
| 32 | Corsym Suspension | 3,500 | No | ++++ |
| 33 | Agarol Laxative Liquid | 2,700 | No | ++++ |
| 34 | Natural Unpasteurized Honey | 22,850 | No | ++++ |
| 35 | PEG 6-32/Carageenen base (Placebo): Sterling Pat #5,200,479 | 16,500 | Yes | −(Phase separation) |
| 36 | Carbomer/Glyc/Sorb: Ex #24 (Placebo), Nestec Pat #5,300,302 | 400 | No | ++++ |
| 37 | Carbomer/Glyc/Sorb/NaOH: Ex #31 (Placebo), Nestec Pat #5,300,302 | Yes | Yes | −− |

*Viscosity measurements done by Brookfield Viscometer, Model BVII, using 'C' spindle at 20 rpm and 20 deg C. except in Nos. 8 & 17, where the 'C' spindle could not be used due to instrument error. The viscosity results shown above are extrapolated from measurements using 'D' spindle.
**Ease of administration is demonstrated through the extrudability of the product from tube onto spoon and then measurability/spreadibility of the product in the spoon, as discussed in the text. Grades '+' to '+++' indicate the products have acceptable extrudability/measurability, whereas product marked '++++' behave like a thick liquid which has a tendency to spill off the spoon on overfilling. Products marked '−' indicate the products do not extrude as uniform gel and also do not have spreading characteristics.

A Summary of the Results of Table 1 is as follows:

(a) The test samples (S.N. 21–31) all had a viscosity when made within the range of 13,500–45,000 at 20 degrees C and 20 rpm. Reference sample S.N. 32, 33, and 36 all had very low viscosity, below 3500 cps.

(b) The test samples all had semisolid characteristics. Reference samples S.N. 32–34 and 36 did not. Viscosity was independent of yield value (semi-solid character) so that a product with the same viscosity can be distinguished as a liquid or semi-solid.

(c) The test samples all rated "+" to "+++" for ease of administration (extrudability spreadability). The samples of S.N. 21–31 have a semi-solid gel-like consistency which can be squeezed out of a tube to the spoon. However, they are thick and the leveling is somewhat slow. This represents an intermediate level of ease of administration and measurability of dosage by spoon-leveling indication. Reference samples S.N. 35 and 36 lacked ease of administration. Ease of administration was also observed to be a characteristic somewhat independent of the other measured characteristics. For example, it may be difficult to administer a unit dose of a thick liquid because the liquid will dribble from the container instead of extrude as a cohesive mass.

TABLE 2

SPILL RESISTANCE DATA

| No. | Product/Base Composition | Time to Spill (min) | | | Non-Spill Characteristics |
|---|---|---|---|---|---|
| | | On Vibration | On Inversion | On Tilting at 90° | |
| A. Test Samples (From Ross Patent Application) | | | | | |
| 21 | PEG/PG base w/Pseudoephed. | 15 | >20 | 1:30 | yes |
| 22 | CMC/PG/Glyc base w/APAP | >60 | 2:40 | 3:51 | yes |
| 23 | Carbomer/NaOH base w/DMH Br | 30 | >20 | 0:40 | yes |
| 24 | CMC/Glyc/Hyd. Glucose base (Placebo) | >60 | 3:40 | 0:58 | yes |
| 25 | CMC/HPMC/Sorbitol base (Placebo) | >60 | >20 | 7 | yes |
| 26 | CMC/Hyd. Glucose base (Placebo) | >60 | 4:10 | 0:56 | yes |
| 27 | CMC base (Placebo) | >60 | 0:31 | 0:22 | yes |
| 28 | CMC/Glyc/MCC/Sorb. base w/Acyclovir | >60 | >20 | >20 | yes |
| 29 | CMC/MCC base (Placebo) | >60 | 0:27 | 0:20 | yes |
| 30 | CMC Base (Placebo) | >60 | >1:15 | 0:45 | yes |
| 31 | CMC PEG Base (Placebo) | >60 | >20 | >20 | yes |
| B. Reference Samples (commercial products or patented examples) | | | | | |
| 32 | Corsym Suspension | 1 | Immediately | Immediately | no |
| 33 | Agarol Laxative Liquid | 0.5 | Immediately | Immediately | no |
| 34 | Natural Unpasteurized Honey | 31 | Immediately | Immediately | no |
| 35 | PEG6-32/Carageenen base (Placebo) Sterling #5,288,479 | 33 | Immediately | 0:11 | no |
| 36 | Carbomer/Glyc/Sorb base: Ex #24 (Placebo) Nestec #5,300,302 | Immediately | Immediately | Immediately | no |
| 37 | Carbo./Glyc/Sorb/NaOH base: Ex #31 (placebo) Nestec #5,300,302 | >60 | >20 | 15 | yes, but too stiff |

Equipment Used: Lab Shaker, Model: BURREL WRIST SHAKER, modified to provide horizontal shaking.
Frequency: 28 per minute
Speed setting: Amplitude: Speed #1:0.5", #2:0.75, #3:1:0, #4:1.25, #5:1.5
Vibrating Time: 10 minutes on each speed beginning from speed #2
Spoon: White plastic spoon round, deep (dia. = 1½" (4 cm) depth. = 7/16" (1.2 cm) with 8 ml capacity.
Inversion and tilting resistance were monitored for 20 minutes.

The results of Table 2 are summarized as follows: The Ross test samples all had non-spill characteristics. Reference samples S.N. 32–36 lacked non-spill characteristics and lacked spill resistance. The characteristics were observed to be largely independent of those reported in Table 1. In particular, for the test samples, the spill start time on vibration was 15 minutes or more, the spills time on inversion was half a minute or more, and the spill start time on tilting at 90 degrees was at least about 30 seconds. The only prior art reference sample that matched this non-spill characteristic was S.N. 37, but it was too stiff for ease of administration (see above).

a) By Vibration: The Ross examples are non-spilling for as much as 15–60 minutes at a shaking speed of 1.5" amplitude w/28 per sec. frequency. In contrast, the marketed products like Corsym (thick suspension), Agarol Laxative Liquid (gel like product), and natural honey tend to spill-off the spoon in less than one to about 30 minutes.

b) By Inversion and Tilting: Many of the Ross test non-spill base products do not spill off the spoon when inverted upside down for as long as 20 minutes, whereas most of the other prior art samples spill off immediately. It was also observed that the test products do not leave residual co tent of the drug product on the spoon, and are not likely to do so when ingested by mouth. This be correlated to the assurance of full dosage administration. In contrast, the thick liquids do not come off cleanly.

As to S.N. 35 (Gorman et al.), the preparation when completed as per the process mentioned in patent does not form a uniform gel. Instead, water starts separating out on storage within few hours. This renders the product not suitable for uniform dosage when the active component will be incorporated, nor is it physically stable. Also, the spill resistance qualities are not met, with special reference to vibration and invertibility. This is different than the qualities covered for the non-spill formulations of the invention.

As to Tachon et. al., S.N. 36 turned out to be a thick liquid and not a semisolid gel, and it lacked spill-resistance as claimed here. S.N. 37 on the other hand yielded a very stiff consistency product which is not easily squeezable from a tube/dispenser and is also non-spreading. Thus this product is inconsistent, and is not easy to administer or measure as to dose.

CONCLUSION: Non-spill formulations according to the Ross invention and the prior art products exhibit particular rheological properties which may be measured as a proxy for administration to dexterity-impaired patients. The test methods described herein are a useful way to determine whether a formulation is suitable for use as a spill-resistant formulation according to the invention, as a non-spill formulation or otherwise. Examples 21–31 are very thick, and examples 32–37 leave other properties that make them unsuitable as a drug delivery system for children and geriatric and motor-disordered patients. These patients find it difficult to keep the hands steady and hence are likely to spill the drug product from the spoon before ingesting. In formulations according to the Ross application, the non-spill base and pharmaceutical formulations offer an absence of spilling despite invertibility.

Example 38–45

In these experiments, spill resistant formulations were prepared containing dextromethorphan hydrobromide (DM), guafenesin (GU), acetaminophen (AC), or pseudoephedrine hydrochloride (PE), in a cellulose-based gel and in a carbomer gel according to the invention. The formulations are given in Table 3.

As can be seen from Table 4, the inventive formulations are semi-solids, unlike the liquid formulations of the prior art. The inventive formulations have very high spreadability,

TABLE 3

| INGREDIENT % | EXAMPLES | | | | | | | |
|---|---|---|---|---|---|---|---|---|
| | 38 | 39 | 40 | 41 | 42 | 43 | 44 | 45 |
| Active | DM | GU | AC | PE | DM | GU | AC | PE |
|  | 0.30 | 2.00 | 3.20 | 0.60 | 0.30 | 2.00 | 3.20 | 0.6 |
| Sodium Carboxy-methylcellulose | 0.90 | 0.90 | 0.90 | 0.90 | | | | |
| Microcrystalline cellulose | 0.90 | 0.90 | 0.90 | 0.90 | | | | |
| Propylene glycol | | | | | 25.00 | 25.00 | 25.00 | 25.00 |
| Carbopol 974 | | | | | 0.50 | 0.25 | 0.25 | 1.00 |
| Glycerin | 30.00 | 30.00 | 30.00 | 30.00 | 50.00 | 50.00 | 50.00 | 50.00 |
| FD&C Yellow #6 | 0.01 | 0.01 | 0.01 | 0.01 | | | | |
| FD&C Red #40 | | | | | 0.005 | 0.005 | 0.005 | 0.005 |
| Sodium saccharin | 0.30 | 0.30 | 0.30 | 0.30 | | | | |
| Methyl paraben | 0.20 | 0.20 | 0.20 | 0.20 | 0.22 | 0.22 | 0.22 | 0.22 |
| Sorbitol 70% | 10.00 | 10.00 | 10.00 | 10.00 | | | | |
| Purified water | 57.39 | 55.69 | 54.49 | 57.09 | 23.975 | 22.525 | 21.325 | 23.175 |
| pH | 6.08 | 6.06 | 6.08 | 6.41 | 6.72 | 6.63 | 6.55 | 6.25 |
| Storage Data | | | | | | | | |
| Viscosity (initial) | 11950 | 11100 | 12175 | 11975 | 7050 | 9550 | 9800 | 10625 |
| Viscosity (40°) | 20560 | 22250 | 9520 | 19354 | 8370 | 9350 | 8650 | 12100 |

Each of these formulations had suitable characteristics of viscosity, spill-resistance, and ease of administration. They were semi-solids. They were freer-flowing gels than the compositions of Ross. They all had pH between about 6 and about 7. Examples 42–45 were essentially free from sodium except for small quantities of sodium hydroxide used to adjust the pH.

In addition, the formulations were subjected to stability testing for several months at room temperature and accelerated stability conditions with elevated temperature and elevated humidity (40 degrees C, 75% relative humidity). In all cases, the formulations were homogeneous at the outset and after stability testing. Viscosity remained suitably constant. Table 3 gives the viscosity data for stored formulation after storage for 3 months at elevated temperature (40 degrees C) and 75% humidity.

An additional unexpected advantage of Example 44 was that the Carbopol had a very effective taste-masking effect, making the formulation palatable despite the bitterness of acetaminophen. This feature permits the avoidance of other taste-masking agents.

TABLE 4

| No. | Active Agent | Thickener | Spill time (sec) 90° | Invert | Spreadability | Semisolid? |
|---|---|---|---|---|---|---|
| 38 | DM | CMC/MCC | 3 | 4 | +++++ | Yes |
| 39 | GU | | 3 | 4 | +++++ | Yes |
| 40 | AC | | 2 | 3 | +++++ | Yes |
| 41 | PE | | 2 | 3 | +++++ | Yes |
| 42 | DM | Carbopol | 1 | 2 | +++++ | Yes |
| 43 | GU | | 2 | 3 | +++++ | Yes |
| 44 | AC | | 2 | 3 | +++++ | Yes |
| 45 | PE | | 2 | 3 | +++++ | Yes |

Spreadability is given on a scale where: −means very stiff semi-solid, +means less stiff semi-solid, 2+, 3+, 4+, and 5+ indicate increasing spreadability.

at least as high as honey. They do not spill from a spoon immediately on tilting or inversion, as do the liquids, but they do come off within several seconds, much faster than the non-spill formulations of Ross.

In addition, the formulations were tested at high frequency vibration similar to the tremors of Parkinsonian patients. At amplitudes of 1 to 2 inches, and frequency of 120–240 per minute (4/sec), the inventive formulations do not spill. This spill-resistance is better than honey at room temperature.

Each reference cited herein is incorporated by reference in its entirety as if specifically incorporated by reference. The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. A method for producing a spill-resistant pharmaceutical formulation, comprising combining a per-unit dose effective amount of a pharmaceutical agent with vehicle components comprising a liquid base and a thickening agent, testing the formulation for acceptance critera for a formulation that can be easily squeezed from a container into a receptacle, measure, and administered orally without spilling the composition from the container or the receptacle, and accepting a formulation that satisfies the acceptance criteria, the acceptance critera comprising:

viscosity within the range equivalent to 5000–45,000 cps using a Brookfield Viscometer with a 'C' spindle with Helipath movement at 20 RPM and 20–25° C., viscometric yield value of a semi-solid, ease of administration comprising (a) extrudability under light manual squeezing from a squeezable container, and (b) spreadability in a spoon bowl measured by extruding the formulation into a spoon bowl and determining whether the material spreads to the edges of the spoon bowl sufficiently quickly for accurate measurement, spill resistance in the spoon bowl during at least one test period comprising vibrations for at least about 30 seconds, inversion for at least about 20 seconds, and tilting for at least about one second, while monitoring whether the product spills from the spoon, mutual compatibility of the components such that they do not separate, and storage stability during storage for an extended period of time for at least one month.

2. A method according to claim 1, wherein the test spoon is plastic and the test period for vibrations is at least about one minute, the test period for inversion is at least about 30 seconds, and the test period for tilting is at least about 20 seconds.

3. A method according to claim 1, wherein the spreadability is such that the formulation spreads to the edge of the spoon within about five seconds.

4. A method according to claim 1, wherein the liquid base is in an amount of about 45 weight-percent to about 95 weight-percent, comprising a palatable solvent, selected from the group consisting of water, propylene glycol, polyethylene glycol, glycerin, and mixtures thereof, and the thickening agent is in an amount up to about 55 weight-percent, and is selected from the group consisting of starch, modified starch, sodium carboxymethyl cellulose in an amount of less than about 2%, microcrystalline cellulose, hydroxypropyl cellulose, other cellulose derivatives, acacia, tragacanth, pectin, gelatin, polyethylene glycol, and water-soluble carboxyvinyl polymers in a concentration of less than 1%.

5. A method according to claim 1, comprising testing a vehicle without the pharmaceutical agent for at least one of the acceptance criteria, combining the pharmaceutical agent with the vehicle, and then testing the formulation for all acceptance criteria.

6. The method according to claim 1, wherein the test spoon is plastic and the test period for vibrations is at least about thirty seconds, and the test period for inversion and for tilting is at least about 1 second.

7. A method according to claim 1, wherein the spreadability is at least as great as honey.

8. A method according to claim 1, further comprising varying the components and/or concentrations of theta liquid base, the thickening agent, and/or the pharmaceutical agent, to prepare a series of formulations.

9. method for producing a spill-resistant pharmaceutical formulation for oral administration from a squeezable container, comprising combining a per-unit dose effective amount of a pharmaceutical agent in a suitable vehicle comprising a liquid base and a thickening agent, testing the formulation for acceptance criteria for a formulation that can be by easily squeezed from the container into a receptacle, measured and administered orally without spilling the composition from the container or the receptacle, and accepting a formulation that satisfies the acceptance criteria, the formulation consisting of mutually compatible components and having the following properties:

an initial viscosity within the range of about 7,500 to about 12,500 cps using a Brookfield Viscometer with a "C" spindle with Helipath movement at a spindle speed of 20 rpm and 20–25° C., a viscometric yield value of a semi-solid, a spill resistant consistency permitting the composition to be squeezed by light manual pressure through a channel of about 1–1.5 mm, to spread in a spoon bowl sufficiently quickly for accurate measurement, and to remain in the spoon bowl without spilling for at least about one second and less than about 20 seconds on spoon tilting at 90 degrees, and for at least about 30 seconds upon spoon vibration at a frequency of about 120/minute, homogeneity such that the components do not separate under conditions of use, and a storage stability such that the foregoing properties are retained for at least three months of storage at elevated temperature, with viscosity remaining within a range of 50% less to 100% more than the initial viscosity, wherein said thickening agent comprises components selected from the group consisting of celluose derivatives in an amount of less than about 2 weight % by volume, and water-soluble cart oxyvinyl polymer in an amount less than 1 weight % by volume.

10. A method for producing a spill-resistant pharmaceutical formulation, comprising combining a per-unit dose effective amount of a pharmaceutical agent with vehicle components comprising a liquid base and a thickening agent, testing the formulation for acceptance criteria for a formulation that can be easily squeezed from a container into a receptacle, measured, and administered orally without spilling the composition from the container or the receptacle, and accepting a formulation that satisfies the acceptance criteria, the acceptance criteria comprising:

viscometric yield value of a semi-solid, ease of administration comprising (a) extrudability under light manual squeezing from a squeezable container, and (b) spreadability in a spoon bowl measured by extruding the formulation into spoon bowl and determining whether the material spreads to the edges of the spoon bowl sufficiently quickly for accurate measurement, spill resistance in the spoon bowl during at least one test period comprising vibrations for at least about 30 seconds, inversion for at least about 20 seconds, and tilting for at least about one second, while monitoring whether the product spills from the spoon, mutual compatibility of the components such that they do not separate, storage stability during storage for an extended period of time for at least one month, and wherein said thickening agent comprises components selected from the group consisting of celluose derivatives in an amount of less than about 2 weight % by volume, and water-soluble carboxyvinyl polymer in an amount less than 1 weight % by volume.

11. A method of testing a spill-resistant pharmaceutical formulation for acceptance criteria a formulation that can be easily squeezed from a container into a receptacle, measured, and administered orally without spilling the composition from the container or the receptacle, the testing comprising, without regard to order, the steps of:

combining per-unit dose effective amount of a pharmaceutical agent with vehicle components comprising a liquid base and a thickening agent, measuring initial viscosity, to determine whether the viscosity is within the range equivalent to 5000–45,000 cps using a Brookfield Viscometer with a 'C' spindle with Helipath movement at 20 RPM and 20–25° C., measuring yield value, extruding the formulation into a spoon from a container through a 1 to 5 mm orifice, observing the spreading/leveling characteristic of the formulation in the spoon bowl, measuring spill resistance of the formulation in a spoon bowl by
- vibrating the spoon bowl for at least about 30 seconds,
- inverting the spoon bowl for at least about 20 seconds, and/or
- tilting the spoon bowl for at least about one second, and
- monitoring whether the product spills from the spoon, and measuring viscosity after storing at elevated temperature for at lease one month.

12. A method of testing according to claim 11, further comprising determining the viscometric yield value is that of a semi-solid.

13. A method of testing according to claim 11, wherein the extruding comprises extruding under light manual squeezing from a squeezable container.

14. A method of testing according to claim 11, wherein the observing consists of determining spreadability in a spoon bowl measured by extruding the formulation into a spoon bowl and determining whether the material spreads to the edges of the spoon bowl sufficiently quickly for accurate measurement.

15. A method of testing according to claim 11, wherein the formulation does not start to spill until after about 30 seconds when vibrated at a frequency of about 2–8 per second, and an amplitude up to about 1 inch.

16. A method of testing according to claim 11, wherein the spill start time on spoon inversion is at least about 20–30 seconds for a plastic 8 ml spoon, longer than for a syrup, and within about 1–20 seconds on spoon tilting at 90 degrees.

17. A method of testing according to claim 11, further comprising determining mutual compatibility of the components such that they do not separate.

18. A method of testing according to claim 11, further comprising measuring storage stability during storage for at least one month.

19. A method of testing according to claim 11, wherein the viscosity is in the range equivalent to 7000–25,000 cps.

20. A method of testing according to claim 11, wherein the viscosity is in the range equivalent to 7000–12,500 cps.

21. A method according to claim 1, wherein the viscosity is in the range equivalent to 7000–25,000 cps.

22. A method according to claim 1, wherein the viscosity is in the range equivalent to 7000–12,500 cps.

* * * * *